United States Patent [19]
Heim et al.

[11] Patent Number: 5,560,352
[45] Date of Patent: Oct. 1, 1996

[54] ANESTHESIA PROTOCOL SYSTEM AND METHOD OF CONTROLLING THE SAME

[75] Inventors: Werner Heim, Herrenberg; Joachim Koeninger, Eutingen; Christian Hickl, Stuttgart, all of Germany

[73] Assignee: Hewlett-Packard Company, Palo Alto, Calif.

[21] Appl. No.: 217,315

[22] Filed: Mar. 24, 1994

[30] Foreign Application Priority Data

Nov. 16, 1993 [DE] Germany ............................ 43 39 154.0

[51] Int. Cl.$^6$ ................................................. A61M 15/00
[52] U.S. Cl. ................................. 128/203.12; 128/204.21
[58] Field of Search ........................ 128/203.12, 204.21, 128/204.23, 205.23; 364/413.01, 413.02, 413.03, 413.05

[56] References Cited

U.S. PATENT DOCUMENTS

| | | | |
|---|---|---|---|
| 3,513,834 | 5/1970 | Suzuki et al. | 128/731 |
| 3,565,080 | 2/1971 | Ide | 128/782 |
| 4,111,198 | 9/1978 | Marx et al. | 364/413.01 |
| 4,347,851 | 9/1982 | Jundanian | 364/413.03 |
| 4,737,912 | 4/1988 | Ichikawa | 364/413.02 |
| 4,853,521 | 8/1989 | Claeys et al. | 364/413.03 |
| 5,003,985 | 4/1991 | White et al. | 364/413.03 |
| 5,140,519 | 8/1992 | Friesdorf et al. | 364/413.03 |
| 5,231,981 | 8/1993 | Scheiber et al. | 128/205.23 |
| 5,331,549 | 7/1994 | Crawford, Jr. | 364/413.01 |
| 5,333,106 | 7/1994 | Lanpher et al. | 364/413.01 |
| 5,392,209 | 2/1995 | Eason et al. | 364/413.01 |

FOREIGN PATENT DOCUMENTS

| | | |
|---|---|---|
| 457000A2 | 3/1991 | European Pat. Off. . |
| 91/09372 | 12/1990 | WIPO . |

Primary Examiner—Aaron J. Lewis

[57] ABSTRACT

In an anesthesia protocol system, vital parameters and medication quantities are stored in a first data base in the form of real time curve signal values, said first data base being organized like a ring buffer. Typically, trend curve signal values are derived from the stored real time curve signal values, and an anesthesia protocol is produced automatically on the basis of these trend curve signal values.

In order to simplify the operability of the anesthesia protocol system and to enhance the information content of the anesthesia protocol, a snapshot input device for activating a snapshot function is provided, a processing unit responding to the actuation of said snapshot input device for reading from the first data base the real time curve signal values which are assigned to a specific snapshot time domain and for storing them in the second data base as snapshot curve signal values, said second data base being not organized in the form of a ring buffer. The anesthesia protocol is produced on the basis of the trend curve signal values as well as on the basis of the snapshot curve signal values.

16 Claims, 2 Drawing Sheets

5,560,352

ANESTHESIA PROTOCOL SYSTEM AND METHOD OF CONTROLLING THE SAME

FIELD OF THE INVENTION

The present invention refers to an anesthesia protocol system for automatically producing anesthesia protocols as well as to a method of controlling an anesthesia protocol system.

DESCRIPTION OF THE PRIOR ART

In all hospitals it has been common practice for decades that anesthesia protocols are manually recorded by the anesthetist in the course of each anesthesia carried out.

A typical anesthesia protocol includes two areas above the time axis, viz. an upper area indicative of the variation with time of the medication, i.e. the administration of medicaments e.g. in absolute amounts or, in the case of anesthetics, also in percentages of the respiratory gas, and a lower area of the anesthesia protocol within which the socalled vital parameters are recorded.

The typical content of an anesthesia protocol comprises the following information: the operating area, i.e. the area of the patient's body which has been operated on; the manner in which the patient was positioned during the operation, e.g. laid on his back, laid on his stomach, etc.; the technical means used for the anesthesia, viz. gas monitors as well as measuring instruments for the electrocardiogram, for $CO_2$, for $SaO_2$, for the invasive or the non-invasive blood pressure, for the central venous pressure, etc.; the type of artificial respiration or ventilation, viz. the spontaneous respiration (the patient breathes himself), the assisted, viz. machine-assisted respiration, such as IPPV (intermittent positive pressure ventilation), PEEP (the kind of artificial respiration which holds the pressure on a specific level during expiration), etc..

In this lower area of the anesthesia protocol, socalled trend curves, viz. e.g. the trend curves of the systolic and of the diastolic blood pressure as well as the trend curve indicating the cardiac rate, are shown by points above the time axis. When the recording is carried out in the form of point curves, symbols for the various trend curves are typically used, said symbols comprising e.g. triangles, dots and the like.

Some doctors prefer a tabular reproduction of numerical values instead of such reproductions in the form of curves.

Furthermore, in the anesthesia protocols made by hand, socalled events or medically relevant occurrences are recorded in the form of numerical marks at the trend curves, and explanations assigned to these numerical marks are added below the protocol.

If, for example, a sudden rise in the patient's blood pressure occurs, a specific number will be recorded by the side of the blood pressure trend curve at the time the rise in blood pressure occurs, and the medical reasons for this rise in blood pressure are indicated in connection with said number at some other point of the protocol.

Furthermore, for statistical purposes as well as for statements of account, the presence of the anesthetist, the length of the actual time of anesthesia, intubation and extubation are recorded in the anesthesia protocol above the time axis, said data being supplemented by the patient's data and data on persons from the medical sphere who were present.

It is obvious that the manual production of an anesthesia protocol is a substantial additional burden for the anesthetist and that especially during a critical condition of the patient, the precise recording of which would be particularly important in connection with an anesthesia protocol, the anesthetist will normally not find time for updating the anesthesia protocol. Hence, especially in situations which are critical from the medical point of view, the anesthetist will be compelled to make the anesthesia protocol from memory after having the patient protected from acute danger, and this will naturally result in an inaccurate or incomplete anesthesia protocol.

Since these problems have been recognized, automatic anesthesia protocol systems or narcosis protocol systems have already been created, which are connected to patient monitors and to an anesthesia machine via interface connections and which automatically procure the patient's vital parameters from the interfaces in the manner explained hereinbelow, store these parameters and combine them so as to obtain an anesthesia protocol in the manner which will be described hereinafter.

FIG. 1 shows a schematic representation of such a known anesthesia protocol system, which has supplied thereto input signals representing at least the socalled vital parameters derived from the patient and supplied to patient monitors MD1, . . . , MDn, the output signals of said monitors being supplied to an interface IF1, IF2. The type of interface is not of decisive importance—neither for the purpose of the present assessment of the prior art nor for the purpose of the present invention. Interfaces which may be used are normal serial interfaces, such as the standard interface RS232, or also special data networks for data of patients, which are offered by the applicant under the name of HP Care-Net-Interface.

The digital curve signals thus produced are stored in a data base by a data processing unit (which is not shown), said data base being organized like a ring buffer having a specific ring buffer length in such a way that, after storage of a number of curve signal values corresponding to the ring buffer length, the respective oldest curve signal value is overwritten by the respective youngest curve signal value. In other words, the data base DB1 has provided therein a plurality of tracks used for storing all the curves and having each a predetermined length, said tracks being repeatedly overwritten with a determinable size like a ring buffer. The data base DB1 has provided therein one "track" for each curve of interest.

In the known system, a monitor MO is provided, which can be controlled by the data processing unit for displaying the real time curves or trend curves.

Furthermore, the known system is capable of automatically producing anesthesia protocols and outputting them either on the monitor or on a printer.

For this purpose, the known system derives from the curves socalled trend curves within the patient monitors. These trend curves are normally values which are derived from the curves and which have a markedly lower time resolution. A trend curve for the systolic and the diastolic blood pressure can, for example, be derived from the curve representing the blood pressure behaviour. Such trend curves are stored in a second data base e.g. with a time resolution of one trend curve signal value per second. The thus obtained point values for the trend curves are then reproduced as a screen display or as a printout of a printer. The curves thus obtained constitute an essential component of the automatically produced anesthesia protocol whose outward appearance largely corresponds to the anesthesia protocol made by hand as far as the representation of the trend curves is concerned.

It is true that also the known system offers the possibility of displaying, in addition to the trend curves,, the current trace of the real time curves on the screen by actuating a socalled zoom key. However, if a part of the real time curves which is of essential importance with respect to medical examination is to be documented permanently, the anesthetist has no other choice than to have the real time curves printed by means of separate curve printers; such a printout of curves can inevitably only be produced from the moment the printer has been switched on so that the typical relevant medical events a short time before a critical condition of the patient occurs cannot be the subject matter of such recording. If the real time curve in question occurred a period of time ago which is longer than the period of time required for storing the signal values over the whole ring buffer length, access to the respective real time curves will no longer be possible, since they have been overwritten in the ring buffer. In view of the fact that, in the known system, the ring buffer is erased when the operation has been finished and in view of the fact that the real time curves in the ring buffer are also automatically overwritten when a specific ring buffer storage time has been exceeded, the real time curves of the vital parameters as well as of possible medication quantities are not permanently available as electronic information in said known system.

SUMMARY OF THE INVENTION

It is the object of the present invention to further develop an anesthesia protocol system of the type mentioned at the beginning in such a way that an improved information content of the anesthesia protocol is achieved although the system is easy to operate.

In accordance with a first aspect of the invention, this object is achieved by an anesthesia protocol system comprising:

- at least one first interface which is used for connecting thereto a patient monitor and by means of which at least one vital parameter of a patient can be detected in the form of a vital parameter signal, said vital parameter being detected by said patient monitor; and/or
- at least one second interface which is used for connecting thereto an anesthesia machine and by means of which a medication quantity measured by said anesthesia machine can be detected in the form of a medication signal;
- a data processing unit sampling the vital parameter signal and/or the medication signal with a first temporal resolution so as to produce real time curve signal values;
- a first data base in which the real time curve signal values are stored, said data base being organized like a ring buffer having a specific ring buffer length in such a way that, after storage of a number of real time curve signal values corresponding to the ring buffer length, the respective oldest real time curve signal value is overwritten by the respective youngest one;
- said processing unit deriving trend curve signal values from said real time curve signal values and storing said trend curve signal values with a second temporal resolution which is lower than said first temporal resolution in a second data base which is not organized like a ring buffer;
- an anesthesia protocol reproduction device adapted to be controlled by said processing unit for reproducing at least one trend curve as part of an anesthesia protocol on the basis of the stored trend curve signal values;
- a snapshot input device for activating a snapshot function;
- said processing unit responding to the actuation of the snapshot input device for carrying out the snapshot function in such a way that the real time curve signal values which are assigned to a specific snapshot time domain are read from the first data base by said processing unit and stored in the second data base as snapshot curve signal values; and
- said anesthesia protocol reproduction device being additionally adapted to be controlled by said processing unit for reproducing the snapshot curve on the basis of the snapshot curve signal values stored in the second data base.

In a preferred embodiment of the anesthesia protocol system of to the invention, the processing unit responds to the actuation of the snapshot input device for defining the temporal position of the snapshot time domain taking as a basis the moment of actuation of the snapshot input device.

In another preferred embodiment of the anesthesia protocol system of to the invention, the processing unit responds to the actuation of the snapshot input device for dating the beginning of the snapshot time domain back into the past by a predetermined period of time taking as a basis the moment of actuation of the snapshot input device.

In another preferred embodiment of the anesthesia protocol system of to the invention, the processing unit is adapted to be actuated by the snapshot input device for defining a snapshot time domain which can be defined freely independently of the moment of actuation of the snapshot input device.

In yet another preferred embodiment of the anesthesia protocol system of to the invention, the snapshot curve signal values are stored in the second data base with a temporal resolution corresponding to the temporal resolution with which the real time curve signal values are stored in the first data base.

In yet another preferred embodiment of the anesthesia protocol system of to the invention, the processing unit produces an empty entry in a data base, with the exception of the first data base, in response to each actuation of the snapshot input device, said entry being assigned with the snapshot curve in question.

In yet another preferred embodiment of the anesthesia protocol system of to the invention, in response to an adequate input entered by an operator, the processing unit overwrites the empty entry with a comment which can be inputted by the operator, and, when the snapshot curve is reproduced by the anesthesia protocol reproduction device, the processing unit reproduces the snapshot curve together with the entry or comment in the anesthesia protocol.

Another object of the present invention is to provide a method of controlling an anesthesia protocol system, which automatically produces anesthesia protocols of high information content without the operator having to invest an excessive amount of time in the production of the anesthesia protocols.

This object is achieved by a method of controlling an anesthesia protocol system, said system comprising:

- at least one first interface which is used for connecting thereto a patient monitor; and/or
- at least one second interface which is used for connecting thereto an anesthesia machine;

a processing unit; and two data bases, said method comprising the steps of:

detecting at least one vital parameter signal on the basis of at least one vital parameter measured by the patient monitor;

and/or detecting at least one medication signal on the basis of at least one medication quantity measured by the anesthesia machine;

sampling the vital parameter signal and/or the medication signal for producing real time curve signal values with a first temporal resolution;

storing the real time curve signal values in a first data base of the two data bases in such a way that, after storage of a number of real time curve signal values corresponding to a ring buffer length of the first data base, the respective oldest real time curve signal value is overwritten by the respective youngest real time curve signal value;

deriving real time curve signal values from said trend curve signal values and storing them in the second one of said data bases with a second temporal resolution which is lower than said first temporal resolution;

reading, in response to actuation of a snapshot input device, the real time curve signal values which are assigned to a specific snapshot time domain from the first data base and storing said real time curve signal values in the second data base as snapshot curve signal values; and reproducing an anesthesia protocol on the basis of the stored trend curve signal values on the one hand and on the basis of the stored snapshot curve signal values on the other.

SHORT DESCRIPTION OF THE DRAWINGS

In the following, a preferred embodiment of the anesthesia protocol system according to the present invention as well as of the method of controlling the same will be explained in detail with reference to the drawings enclosed, in which.

DESCIPTION OF THE PREFERRED
EMBODIMENTS OF THE INVENTION

Figure 1:
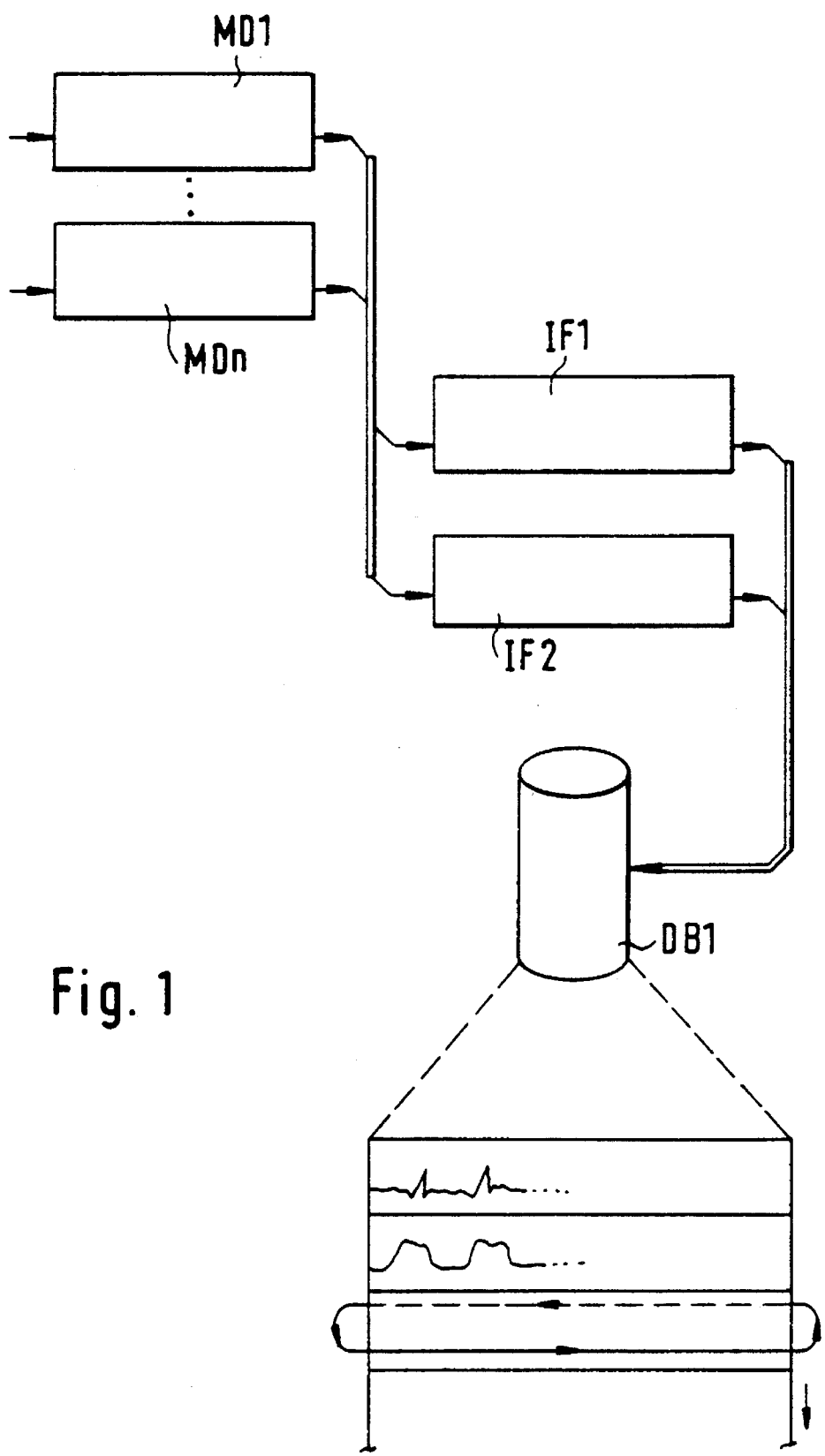
FIG. 1 shows the structural design of a known anesthesia protocol system.
Figure 2:
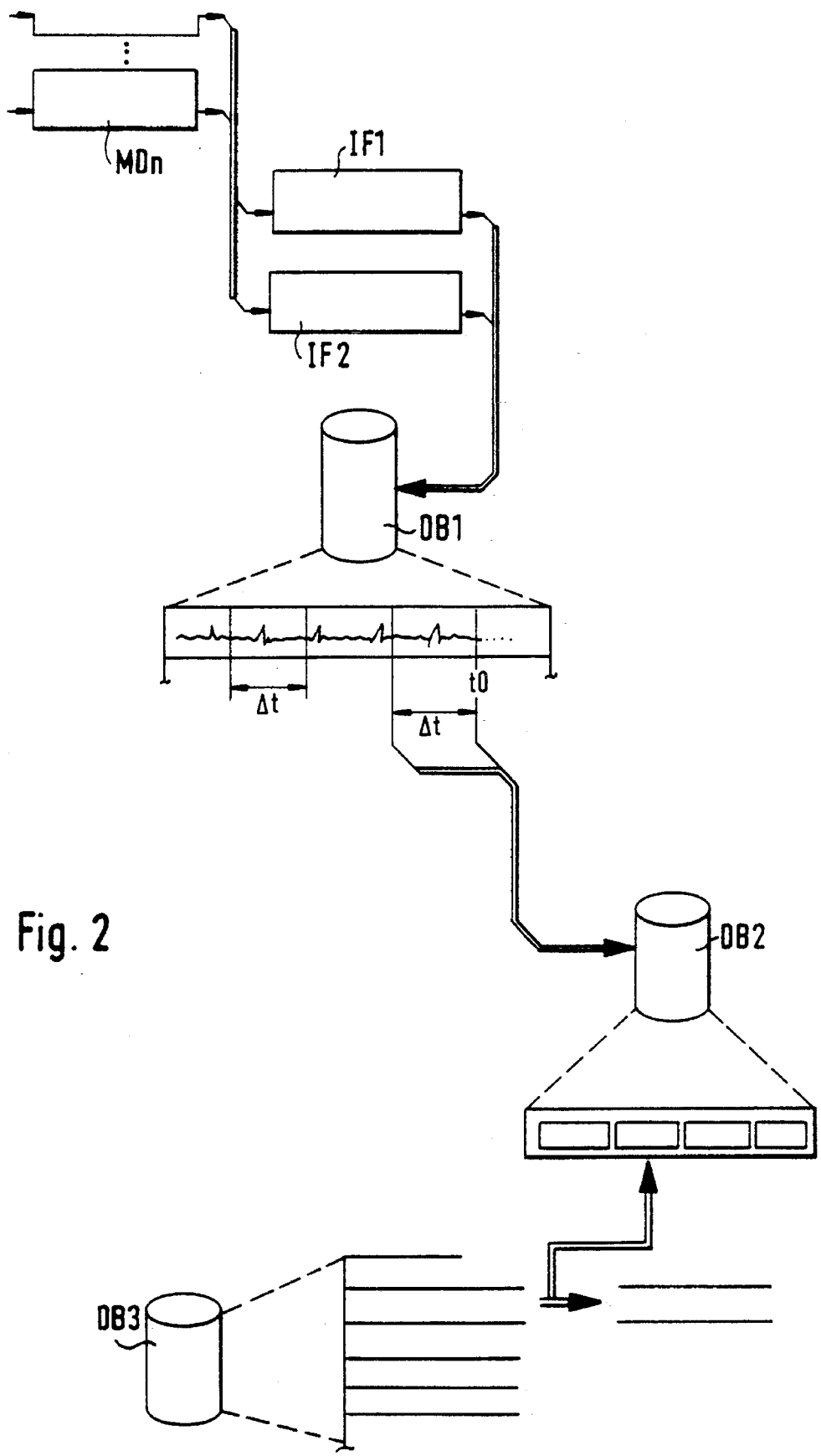
FIG. 2 shows the structural design of an anesthesia protocol system according to the present invention.

The structural design and the mode of operation of the anesthesia protocol system according to the present invention correspond to the structural design and mode of operation of the known system described with reference to FIG. 1, with the exception of the deviations which will be described hereinbelow so that it is not necessary to describe again how the real time signals, which are stored in the first data bank having a structure like a ring buffer, are obtained.

As has already been stated, the real time signals can be vital parameter signals which are detected by a patient monitor MD1 to MDn as well as medication quantities which have been stored by an anesthesia machine via an interface IF1 or IF2 in the data base DB1 in the form of real time signals.

The system according to the present invention is provided with a so called "snapshot" input device in the form of a snapshot key which is connected to the processing unit (not shown). The processing unit responds to the actuation of the snapshot key for reading the real time curve signal values which are assigned to a specific snapshot time domain delta t from the first data base DB1 and storing them in a second data base DB2 in the form of snapshot curve signal values. In contrast to the first data base DB1, the second data base DB2 is not organized like a ring buffer and permits a permanent storage of data.

In connection with one possible mode of operation of the anesthesia protocol system according to the present invention, the beginning of the snapshot time domain delta t is defined—taking as a basis the moment of actuation of the snapshot key—by dating the beginning of the snapshot time domain delta t back into the past by a predetermined period of time of e.g. 30 to 90 seconds taking as a basis the moment of actuation of the snapshot key. Taking this moment as a basis, it is possible to define the end of the snapshot time domain such that it occurs in the past, or at the current moment of the actuation of the snapshot key, or, taking as a basis the moment of actuation of the snapshot key, in the future. When the mode of calculating the snapshot time domain has been determined once, it will always be possible to take the moment of actuation of the snapshot key as a basis and to define the snapshot time domain by simple actuation of a key, whereby each real time curve stored in the data base DB1 will have selected therefrom the data which are to be stored in the second data base DB2. In order to define the above more clearly, it is also pointed out that the snapshot time domain can be used either for selecting a real time signal section of only one real time signal or for transferring time-correspondent signal sections of all real time curves from the first data base DB1 to the second data base DB2.

The respective section of each real time curve defined by the snapshot time domain is stored in the second data base DB2 under the ordering criterion of the current time at which the respective snapshot was taken.

Together with each snapshot an empty entry is produced in a third data base DB3, which is referred to as anesthesia protocol data base, each entry having assigned thereto a snapshot. The anesthetist can overwrite this empty entry with an information, which describes the nature of the medically relevant event, at an arbitrary later time, i.e. for example during a quiet phase of the operation or after the end of the operation. These entries correspond to the "events" which were explained at the beginning with reference to the manually produced anesthesia protocols.

The definition of the snapshot time domain can be modified freely. Deviating from the above-described embodiment, it is, for example, possible to extract the snapshot from a part of the real time curve of the data base which lies completely in the past, but which must, of course, still lie within the area which has not yet been overwritten in the mode of operation of the memory resembling a ring buffer.

The anesthesia protocols which are automatically produced by the anesthesia protocol system according to the present invention can be reproduced in two different modes. On the one hand, it is possible to effect a screen display of the anesthesia protocol. On the other hand, a printout of the anesthesia protocol can be produced.

Preferably, a printed anesthesia protocol has, in turn, two sections, the first section corresponding to the normal anesthesia protocol which has been produced automatically on the basis of the trend curves. The second section comprises a socalled graphics report including the respective snapshots, i.e. domain sections of the real time curves, under the caption of the entry made by the anesthetist.

We claim:

1. An anesthesia protocol system for use with a patient monitor and an anesthesia machine comprising:

a first interface for connecting to patient monitor and for detecting at least one vital parameter of a patient vital parameter signal detected by patient monitor;

a second interface for connecting to an anesthesia machine and for detecting a medication quantity in the form of a medication signal measured by anesthesia machine;

a data processing unit for sampling the patient vital parameter signal and the medication signal with a first temporal resolution so as to produce real time curve signal values;

a first data base responsive to the real time curve signal values for storing the real time curve signal values, said data base being effectively a ring buffer having a specific ring buffer length such that, after storage of a number of real time curve signal values corresponding to the ring buffer length, the respective oldest real time curve signal value is overwritten by the respective newest real time curve signal value;

said data processing unit deriving trend curve signal values from said real time curve signal values and storing said trend curve signal values with a second temporal resolution which is lower than said first temporal resolution in a second data base which is not organized like a ring buffer;

an anesthesia protocol reproduction device adapted to be controlled by said data processing unit for reproducing at least one trend curve as part of an anesthesia protocol on the basis of the stored trend curve signal values;

a snapshot input device for activating a snapshot function for analyzing a signal at an instant of time;

said data processing unit responding to actuation of the snapshot input device for carrying out the snapshot function in such a way that the real time curve signal values which are assigned to a specific snapshot time domain are read from the first data base by said data processing unit and stored in the second data base as snapshot curve signal values; and said anesthesia protocol reproduction device being additively adapted to be controlled by said data processing unit for reproducing the snapshot curve on the basis of the snapshot curve signal values stored in the second data base.

2. An anesthesia protocol system according to claim 1, wherein the data processing unit responds to actuation of the snapshot input device for defining a temporal position of the specific snapshot time domain, taking as a basis the moment of actuation of the snapshot input device.

3. An anesthesia protocol system according to claim 2, wherein the data processing unit responds to actuation of the snapshot input device for dating the beginning of the snapshot time domain back into the past by a predetermined period of time, taking as a basis the moment of actuation of the snapshot input device.

4. An anesthesia protocol system according to claim 1, wherein the data processing unit is adapted to be actuated by the snapshot input device for defining a snapshot time domain which can be defined freely independently of the moment of actuation of the snapshot input device.

5. An anesthesia protocol system according to claim 1, wherein the snapshot curve signal values are stored in the second data base with a temporal resolution corresponding to the first temporal resolution with which the real time curve signal values are stored in the first data base.

6. An anesthesia protocol system according to claim 1, wherein the data processing unit produces an empty entry in a data base, with the exception of the first data base, in response to each actuation of the snapshot input device, said entry being assigned with the snapshot curve signal values in question.

7. An anesthesia protocol system according to claim 6, wherein, in response to an adequate input entered by an operator, the data processing unit overwrites the empty entry with a comment which can be inputted by the operator, and wherein, when the snapshot curve signal values are reproduced by the anesthesia protocol reproduction device, the data processing unit reproduces the snapshot curve signal values together with the entry or comment in the anesthesia protocol.

8. A method of controlling an anesthesia protocol system including a patient monitor, an anesthetic machine, a first interface connected to a patient monitor;

a second interface connected to an anesthesia machine;

a processing unit; and two data bases, said method comprising the steps of:

detecting at least one vital parameter signal on the basis of at least one vital parameter measured by the patient monitor;

detecting at least one medication signal on the basis of at least one medication quantity measured by the anesthesia machine;

sampling the vital parameter signal and the medication signal producing real time curve signal values with a first temporal resolution;

storing the real time curve signal values in a first data base of the two data bases in such a way that, after storage of a number of real time curve signal values corresponding to a ring buffer length of the first data based the respective oldest real time curve signal value is overwritten by the respective newest real time curve signal value;

deriving real time curve signal values from trend curve signal values and storing them in the second one of said data bases with a second temporal resolution which is lower than said first temporal resolution;

reading, in response to actuation of a snapshot input device, the real time curve signal values which are assigned to a specific snapshot time domain from the first data base and storing said real time curve signal values in the second data base as snapshot curve signal values; and reproducing an anesthesia protocol on the basis of the stored trend curve signal values and on the basis of the stored snapshot curve signal values.

9. An anesthesia protocol system for use with at least one of a patient monitor machine for deriving a patient vital parameter signal and an anesthesia machine for deriving a medication quantity signal comprising:

interface means for connection to at least one of a patient monitoring machine or an anesthesia the machine for detecting at least one of the derived signals;

a data processing unit for sampling at least one of the derived signals;

said data processing unit deriving real time curve signal values having a first temporal resolution and that are overwritten by a respective newest real time curve signal values;

a first data base responsive to the real time curve signal values for storing the real time curve signal values, said data base being effectively a ring buffer having a specific ring buffer length such that, after storage of a number of real time curve signal values corresponding to the ring buffer length, the respective oldest real time curve signal value is overwritten by the respective newest real time curve signal value;

a second data base which is not organized like a ring buffer;

said data processing unit deriving trend curve signal values from said real time curve signal values and storing said trend curve signal values with a second temporal resolution which is lower than said first temporal resolution in the second data base;

an anesthesia protocol reproduction device adapted to be controlled by said data processing unit for reproducing at least one trend curve as part of an anesthesia protocol on the basis of the stored trend curve signal values;

a snapshot input device for activating a snapshot function for analyzing a signal at an instant of time;

said data processing unit responding to actuation of the snapshot input device for carrying out the snapshot function in such a way that the real time curve signal values which are assigned to a specific snapshot time domain are read from the first data base by said data processing unit and stored in the second data base as snapshot curve signal values; and said anesthesia protocol reproduction device being additively adapted to be controlled by said data processing unit for reproducing the snapshot curve on the basis of the snapshot curve signal values stored in the second data base.

10. An anesthesia protocol system according to claim 9, wherein the data processing unit responds to actuation of the snapshot input device for defining a temporal position of the specific snapshot time domain, taking as a basis the moment of actuation of the snapshot input device.

11. An anesthesia protocol system according to claim 10, wherein the data processing unit responds to actuation of the specific snapshot input device for dating the beginning of the snapshot time domain back into the past by a predetermined period of time, taking as a basis the moment of actuation of the snapshot input device.

12. An anesthesia protocol system according to claim 9, wherein the data processing unit is adapted to be actuated by the snapshot input device for defining a snapshot time domain which can be defined freely independently of the moment of actuation of the snapshot input device.

13. An anesthesia protocol system according to claim 9, wherein the snapshot curve signal values are stored in the second data base with a temporal resolution corresponding to the temporal resolution with which the real time curve signal values are stored in the first data base.

14. An anesthesia protocol system according to claim 9, wherein the data processing unit produces an empty entry in a data base, with the exception of the first data base, in response to each actuation of the snapshot input device, said entry being assigned with the snapshot curve in question.

15. An anesthesia protocol according to claim 14, wherein, in response to an adequate input entered by an operator, the data processing unit overwrites the empty entry with a comment which can be inputted by the operator, and wherein, when the snapshot curve is reproduced by the anesthesia protocol reproduction device, the processing unit reproduces the snapshot curve together with the entry or comment in the anesthesia protocol.

16. A method of controlling an anesthesia protocol system including (a) at least one of a patient monitor machine for deriving a patient vital parameter signal and an anesthesia machine for deriving a medication quantity signal, (b) an interface arrangement connected to at least one of the machines, (c) a processing unit, and (d) two data bases, the method comprising:

detecting at least one of the derived signals;

sampling the detected signal and producing real time curve signal values with a first temporal resolution;

storing the real time curve signal values in a first data base of the two data bases in such a way that, after storage of a number of real time curve signal values corresponding to a ring buffer length of the first data base, the respective oldest real time curve signal value is overwritten by the respective newest real time curve signal value;

deriving real time curve signal values from trend curve signal values and storing them in the second one of said data bases with a second temporal resolution which is lower than said first temporal resolution;

reading, in response to actuation of a snapshot input device, the real time curve signal values which are assigned to a specific snapshot time domain from the first data base and storing said real time curve signal values in the second data base as snapshot curve signal values; and reproducing an anesthesia protocol on the basis of the stored trend curve signal values and on the basis of the stored snapshot curve signal values.

* * * * *